United States Patent
Kumar et al.

(10) Patent No.: US 9,938,175 B2
(45) Date of Patent: Apr. 10, 2018

(54) BIO-ASSISTED PROCESS FOR THE TREATMENT AND REGENERATION OF SPENT CAUSTIC

(71) Applicant: Indian Oil Corporation Limited, Bandra (East), Mumbai (IN)

(72) Inventors: Manoj Kumar, Faridabad (IN); Mahendra Pratap Singh, Faridabad (IN); Dheer Singh, Faridabad (IN); Anurag Ateet Gupta, Faridabad (IN); Ravinder Kumar Malhotra, Faridabad (IN)

(73) Assignee: INDIAN OIL CORPORATION LIMITED, Bandra (East) (IN)

( * ) Notice: Subject to any disclaimer, the term of this patent is extended or adjusted under 35 U.S.C. 154(b) by 16 days.

(21) Appl. No.: 15/195,335

(22) Filed: Jun. 28, 2016

(65) Prior Publication Data
US 2017/0369349 A1 Dec. 28, 2017

(30) Foreign Application Priority Data

Jun. 29, 2015 (IN) .................... 2480/MUM/2015

(51) Int. Cl.
| | | |
|---|---|---|
| *B01D 53/84* | (2006.01) | |
| *C02F 3/34* | (2006.01) | |
| *C12N 11/14* | (2006.01) | |
| *C12P 7/62* | (2006.01) | |
| *C02F 3/02* | (2006.01) | |
| C02F 101/10 | (2006.01) | |
| C02F 101/32 | (2006.01) | |
| C02F 101/34 | (2006.01) | |
| C02F 103/36 | (2006.01) | |

(52) U.S. Cl.
CPC ............... *C02F 3/341* (2013.01); *C02F 3/02* (2013.01); *C02F 3/345* (2013.01); *C02F 2101/101* (2013.01); *C02F 2101/32* (2013.01); *C02F 2101/345* (2013.01); *C02F 2101/40* (2013.01); *C02F 2103/365* (2013.01)

(58) Field of Classification Search
CPC .......... B01D 2251/95; B01D 2255/804; B01D 2257/504; B01D 2258/0283; B01D 53/84; C02F 2103/10; C02F 2103/365; C02F 3/341; C02F 3/342; C10G 19/08; C12N 11/14; C12P 7/62; Y02C 10/02
See application file for complete search history.

(56) References Cited

U.S. PATENT DOCUMENTS

| | | |
|---|---|---|
| 5,480,550 A | 1/1996 | Sublette |
| 6,045,695 A | 4/2000 | Janssen et al. |
| 2011/0024351 A1 | 2/2011 | Janssen |

OTHER PUBLICATIONS

Pradeep et al., Biological removal of phenol from wastewaters: a mini review, 2015, Appl. Water Sci., vol. 5, pp. 105-112.
Rajganesh et al., Biotreatment of Refinery Spent Sulfidic Caustics, Mar./Apr. 1995, Biotechnology Progress, vol. 11, Issue 2, pp. 228-230.

*Primary Examiner* — Dirk Bass
(74) *Attorney, Agent, or Firm* — Workman Nydegger

(57) ABSTRACT

The present invention relates to a bio-assisted method for treatment of spent caustic by treating with haloalkaliphilic consortium of bacteria capable of reducing or transforming sulphides, thiols, mercaptans and other sulphur containing compounds, phenols, hydrocarbons, naphthenic acids and their derivatives in spent caustic.

12 Claims, No Drawings

BIO-ASSISTED PROCESS FOR THE TREATMENT AND REGENERATION OF SPENT CAUSTIC

FIELD OF THE INVENTION

The present invention relates to biological treatment and regeneration of spent caustic obtained from hydrocarbon and gas processing installations.

BACKGROUND OF THE INVENTION

Aqueous alkali metal hydroxide solution i.e., caustic is used for removal of various toxicants like sulphides, mercaptans, amines, naphthenic acids, phenols etc. from gaseous and hydrocarbon streams in oil refinery processes. Once these contaminants come in contact and react with caustic solution, it cannot be further utilized and is known as spent caustic. A typical spent caustic may contain about 3-12% of the NaOH with varying but significant quantities of toxic compounds like sulphides, mercaptans, amines, naphthenic acids, phenols, their derivatives, hydrocarbons and few other inorganic and organic compounds. Owing to presence of these contaminants and high salinity and high pH, spent caustics are most difficult of all industrial wastes to dispose properly. Spent caustic is disposed by very expensive and environmentally reactive methods such as high dilutions and then treatment at ETP, deep well injections, incineration, wet air oxidation, humid hydrogen peroxide oxidation etc.

In context of above, biological treatment of spent caustics at atmospheric pressures and temperature would be cheaper and environment friendly alternative to the currently employed treatment methods.

A biological process for the treatment of spent caustics was described by Rajganesh, Sublette, Camp and Richardson, Biotechnology Progress, 1995 (11), 228-230. In this process, sulfides are completely oxidized to sulfate by *Thiobacillus denitrificans*. This paper discloses a process for treatment of spent caustic wherein only sulfides are removed from the spent caustic. Also, the process is required to be performed at low pH of 7.0 wherein said pH is maintained by addition of acid like 10N nitric acid solution. The major drawback of above said process is that only one impurity like sulfides are treated and therefore, additional process is required for the treatment of other impurities like phenols, amines, naphthenic acids, hydrocarbons etc. from spent caustic. Secondly, an additional step of maintaining the pH by addition of 10N nitric acid solution is employed in the process which results into extra cost in terms of chemical requirements for treatment of spent caustic. Moreover, the process includes use of undefined mixture of microbes which are difficult to replicate and takes long time for acclimatization.

U.S. Pat. No. 5,480,550 discloses a biological process for the disposal for caustic waste streams containing inorganic sulfides to effect neutralization of the caustic and oxidation of sulfides to sulfates. The process disclosed in above said patent includes use of flocculated cultures of a sulfide-oxidizing bacterium from the genus *Thiobacillus* and various heterotrophs. The process includes immobilization of the bacteria and use of undefined mixture of microbes which are difficult to replicate. This process suffers from major drawback of immobilizing bacteria by co-culture with at least one floc-forming heterotroph under aerobic conditions to form a flocculated biomass. Secondly, the process of disposal of caustic waste streams is performed at pH of 7.0 and same is maintained by addition of 10N nitric acid solution. Hence, addition of heterotroph and nitric acid results into undesired addition of cost to the disposal process.

U.S. Pat. No. 6,045,695 discloses a process for the biological treatment of spent caustic solution containing sulfides, wherein the solution introduces into an aerobic reactor containing sulfide-oxidizing bacteria, and the sulfides are partly converted to elemental sulfur and partly to sulfate by controlling the redox potential in the reactor at a value below 300 mV (against an Ag/AgCl reference electrode), or below −97 (against reference electrode). The process suffers from disadvantages like the sulfide oxidation is done by using *M. sulfidovorans* which result into formation of thiosulfate. Usually thiosulfate is an undesirable component in waste water. Therefore, it is preferred then to combine the use of *M. sulfidovorans* with bacteria like genus *Thiobacillus* to convert thiosulfate to sulfate and/or sulfur which ultimately results into increase in the cost of disposal of impurities from spent caustic.

US patent application 2001/0024351 discloses a method and apparatus for biologically treating a spent caustic to provide a treated spent caustic, said method comprising the steps of: (a) passing a spent caustic stream comprising water, alkali metal hydroxide and sulfide to a first bioreactor; (b) biologically oxidizing sulfide in the first bioreactor with sulfide-oxidizing bacteria like *thiobacillus* and *thiomicrospira*) to form sulfur and sulfate to provide a partially oxidized spent caustic; (c) passing the partially oxidized spent caustic to a second bioreactor where at least a portion of the partially oxidized spent caustic is further oxidized with sulfide-oxidizing bacteria to generate sulfate from sulfur to provide a treated spent caustic comprising sulfate.

The drawbacks of above said process is that the process requires two bioreactors for treatment of spent caustic resulting into increase in cost. Further additional step of maintaining the pH to 8.5 is required wherein said pH is maintained by addition of acids like hydrochloric acid or sulfuric acid and hence results additional cost for chemical requirements. Moreover, only one impurity is treated like sulfides and therefore, additional process is required for the treatment of other impurities like phenols, amines, naphthenic acids, hydrocarbons etc. from spent caustic.

Pradeep et al. (2015; Appl. water Sci., Vol. 5: 105-112) discloses biological degradation of phenols from waste water using bacteria like *Pseudomonas* and *B. subtilis*. This publication mentions that the optimum pH for biological treatment of phenol is in between 6 to 9. This shows that critical parameters of pH are required to be maintained to perform the degradation process. Here, only one impurity is treated like phenols and therefore, additional process is required for the treatment of other impurities like phenols, amines, naphthenic acids, hydrocarbons etc. from spent caustic.

Therefore, there is a need for an improved method for treating spent caustic which meet effluent discharge standards, and which include minimal step for disposal of all the impurities/contaminants from spent caustic under ambient conditions of pH, temperature and pressure in an effective and economical way. Moreover, such treated spent caustic is required to be re-usable.

SUMMARY OF THE INVENTION

The main embodiment of the present invention provides a bio-assisted method of treating spent caustic using haloalkaliphilic bacterial consortium said method comprises the steps of:

(a) mixing the spent caustic with haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389) and *Lysinibacillus* sp. (MTCC 5666) in a reactor;
(b) maintaining the percentage of saturated oxygen in the reactor initially in the range of 0-20% or 60-100% saturation for 48 hrs followed by saturated oxygen in the range of 60-100% or 0-20% for 24-48 hrs respectively;
(c) carrying out the reaction of steps (i) and (ii) for about 3-5 days; and
(d) obtaining caustic with reduced concentration of sulphides, thiols, other sulphur containing compounds, phenols, hydrocarbons, naphthenic acids and their derivatives.

Another embodiment of the present invention provides a method as herein described wherein the said haloalkaliphilic bacterial consortium in step (a) comprises any three or more bacteria selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389) and *Lysinibacillus* sp. (MTCC 5666).

Another embodiment of the present invention provides haloalkaliphic bacterial consortium used for the treatment of spent caustic to remove sulphides, thiols, other sulphur containing compounds, phenols, hydrocarbons, napthenic acids and their derivatives from the spent caustic, wherein the contaminants in spent caustics under conditions of ambient temperature and pressure.

In another aspect the present invention provides a method of treating contaminants of spent caustic with haloalkaliphic bacterial consortium which are having pH in the range of 8-13 and wherein haloalkaliphic bacterial consortium can tolerate a temperature in the range of 5-60° C.

Another embodiment of the present invention provides a method as herein described wherein the method in step (a) is performed at pH in the range of 8 to 13.

Another embodiment of the present invention provides a method as herein described wherein the method in step (a) is performed above pH 8.

Yet another embodiment of the present invention provides a method as herein described wherein the haloalkaliphilic microbial consortium is present in a concentration of $10^2$ CFU/ml.

Another embodiment of the present invention provides a method as herein described wherein in step (b) the saturated oxygen in the reactor is initially maintained in the range of 0-20% followed by saturated oxygen maintained in the range of 60-100%.

Another embodiment of the present invention provides a method as herein described wherein in step (b) the saturated oxygen in the reactor is initially maintained in the range of 60-100% followed by saturated oxygen is in the range of 0-20%.

Another embodiment of the present invention provides a method as herein described wherein then method is carried out in two reactors then saturated oxygen in the first reactor is maintained at 0-20% or 60-100% followed by saturated oxygen in the second reactor is maintained at 60-100% or 0-20% respectively.

Another embodiment of the present invention provides a method as herein described wherein then method is carried out in single reactor, wherein the saturated oxygen is initially maintained at 0-20% or 60-100% followed by saturated oxygen maintained at 60-100% or 0-20% respectively.

Another embodiment of the present invention provides a method as herein described wherein the haloalkaliphilic bacterial consortium is present in a concentration of at least $10^2$ CFU/ml.

Another embodiment of the present invention provides a method as herein described wherein the haloalkaliphilic bacterial consortium is used in immobilized or free form.

Another embodiment of the present invention provides a method as herein described wherein said method is done either in same reactor by altering the air saturation after certain time or in two series reactor where effluent of one reactor work as influent to another reactor and both reactors has different air saturation level.

Yet another embodiment of the present invention provides method as herein described wherein the method is performed in batch mode as well as continuous mode using continuously stirrer reactor, up-flow reactor and any such suitable continuous mode reactor.

Yet another embodiment of the present invention provides a method as herein described wherein the haloalkaliphilic bacterial consortium are immobilized when the reaction is carried out in continuous mode.

Yet another embodiment of the present invention provides a method as herein described wherein the reaction is carried out in a single reactor or two reactors.

DETAILED DESCRIPTION

While the invention is susceptible to various modifications and/or alternative processes and/or compositions, specific embodiment thereof has been shown by way of example in the drawings and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The tables and protocols have been represented where appropriate by conventional representations, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Definitions

The term "Haloalkalkiphilic bacteria" as used in the context of the present invention means bacteria is able to grow under high alkaline conditions which comprises of high salt as well as high pH which is above pH 8. More specifically such "Haloalkaliphilic bacteria" grow at pH in the range of 8-13. The "Haloalkaliphilic bacteria" have a special mechanisms to survive and grow under salinity and high alkaline pH wherein these bacteria can survive at pH in the range of 8 to 13 and salt concentration of 2-8%.

The term "Haloalkaliphilic consortium" or "Haloalkaliphilic consortium of bacteria or "Haloalkaliphilic bacterial consortium", as used in context of the present invention refers to consortium or mixture of bacteria selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) capable of treating or breaking down contaminants from the spent caustic. The "Haloalkaliphilic consortium" or "Haloalkaliphilic consortium of bacteria or "Haloalkaliphilic bacterial consortium" or "microbial consortium" in the context of present invention could also means a consortium or mixture of any two or more bacteria selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) capable of treating or breaking down contaminants from the spent caustic.

The term "Contaminants" as used in context of present invention refers to all the impurities present in the spent caustic not limited to but including sulphides, thiols, mercaptans and other sulphur containing compounds, phenols, hydrocarbons, naphthenic acids and their derivatives.

The term "Ambient temperature" and "pressure" as used in context of the present invention relates to the temperature and pressure ranging from 20-40° C. and 1-2 bar, respectively.

The term "Hydraulic Retention Time (HRT)" as used in context of the present invention relates to average length of time that a spent caustic remains in the reactor.

The term "Industrial Application" as used in context of the present invention refers to use of treated spent caustic in industrial processes for removal of contaminants from gaseous and hydrocarbon streams in oil refinery processes or may be used for the pH maintenance of the waste water treatment plans or biological processes.

The term "Oxygen saturation" or "percentage of oxygen saturation" as used in context of the present invention refers to relative measure of the amount of oxygen that is dissolved or carried in a given medium. In context of present invention the percentage of oxygen saturation can be extensively varied at the start or initial stage of the treatment as well at the later stage of the treatment, as discussed below:

(i) At the start of the treatment the oxygen saturation can be maintained as low as in the range of 0-20% followed by higher oxygen saturation in the range of 60-100%; or (ii) At the start of the treatment the oxygen saturation can maintained as high as in the range of 60-100% followed by lowering of the oxygen saturation in the range of 0-20%.

As used herein, the terms "Oxygen saturation" or "percentage of oxygen saturation" as used in the context of the present invention have been used interchangeably and are meant to have the same definition and meaning as herein described.

The main embodiment of the present invention provides a bio-assisted method of treating spent caustic using haloalkaliphilic bacterial consortium said method comprises the steps of:

(a) mixing the spent caustic with haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389) and *Lysinibacillus* sp. (MTCC 5666) in a reactor;

(b) maintaining the percentage of saturated oxygen in the reactor initially in the range of 0-20% or 60-100% saturation for 48 hrs followed by saturated oxygen in the range of 60-100% or 0-20% for 24-48 hrs respectively;

(c) carrying out the reaction of steps (i) and (ii) for about 3-5 days; and (d) obtaining caustic with reduced concentration of sulphides, thiols, other sulphur containing compounds, phenols, hydrocarbons, naphthenic acids and their derivatives.

Another embodiment of the present invention provides a bio-assisted method of treating spent caustic using haloalkaliphilic bacterial consortium said method comprises the steps of:

(a) mixing the spent caustic with haloalkaliphilic consortium of any two or more bacteria selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389) and *Lysinibacillus* sp. (MTCC 5666). and nutrient system in a reactor;

(b) maintaining the percentage of saturated oxygen in the reactor initially in the range of 0-20% or 60-100% saturation for 48 hrs followed by saturated oxygen in the range of 60-100% or 0-20% for 24-48 hrs respectively;

(c) carrying out the reaction of steps (i) and (ii) for about 3-5 days; and (d) obtaining caustic with reduced concentration of sulphides, thiols, other sulphur containing compounds, phenols, hydrocarbons, naphthenic acids and their derivatives.

Another embodiment of the present invention provides a method as herein described wherein the said haloalkaliphilic bacterial consortium in step (a) comprises any three or more bacteria selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389) and *Lysinibacillus* sp. (MTCC 5666).

Another embodiment of the present invention provides haloalkaliphic bacterial consortium used for the treatment of spent caustic to remove sulphides, thiols, other sulphur containing compounds, phenols, hydrocarbons, napthenic acids and their derivatives from the spent caustic, wherein the contaminants in spent caustics under conditions of ambient temperature and pressure.

In another aspect the present invention provides a method of treating contaminants of spent caustic with haloalkaliphic bacterial consortium which are having pH in the range of 8-13 and wherein haloalkaliphic bacterial consortium can tolerate a temperature in the range of 5–60° C.

Another embodiment of the present invention provides a method as herein described wherein the method in step (a) is performed at pH in the range of 8 to 13.

Another embodiment of the present invention provides a method as herein described wherein the method in step (a) is performed above pH 8.

Yet another embodiment of the present invention provides a method as herein described wherein the haloalkaliphilic microbial consortium is present in a concentration of $10^2$ CFU/ml.

Another embodiment of the present invention provides a method as herein described wherein in step (b) the saturated oxygen in the reactor is initially maintained in the range of 0-20% followed by saturated oxygen maintained in the range of 60-100%.

Another embodiment of the present invention provides a method as herein described wherein in step (b) the saturated oxygen in the reactor is initially maintained in the range of 60-100% followed by saturated oxygen is in the range of 0-20%.

Another embodiment of the present invention provides a method as herein described wherein then method is carried out in two reactors then saturated oxygen in the first reactor is maintained at 0-20% or 60-100% followed by saturated oxygen in the second reactor is maintained at 60-100% or 0-20% respectively.

Another embodiment of the present invention provides a method as herein described wherein then method is carried out in single reactor, wherein the saturated oxygen is initially maintained at 0-20% or 60-100% followed by saturated oxygen maintained at 60-100% or 0-20% respectively.

Another embodiment of the present invention provides a method as herein described wherein the haloalkaliphilic bacterial consortium is present in a concentration of at least $10^2$ CFU/ml.

Another embodiment of the present invention provides a method as herein described wherein the haloalkaliphilic bacterial consortium is used in immobilized or free form.

Another embodiment of the present invention provides a method as herein described wherein said method is done either in same reactor by altering the air saturation after certain time or in two series reactor where effluent of one reactor work as influent to another reactor and both reactors has different air saturation level.

Yet another embodiment of the present invention provides method as herein described wherein the method is performed in batch mode as well as continuous mode using continuously stirrer reactor, up-flow reactor and any such suitable continuous mode reactor.

Yet another embodiment of the present invention provides a method as herein described wherein the haloalkaliphilic bacterial consortium are immobilized when the reaction is carried out in continuous mode.

Yet another embodiment of the present invention provides a method as herein described wherein the reaction is carried out in a single reactor or two reactors.

Yet another embodiment of the present invention provides haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) capable of reducing or transforming sulphides, thiols, other sulphur containing compounds, phenols, hydrocarbons, naphthenic acids and their derivatives in spent caustic.

Yet another embodiment of the present invention provides two or more haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) capable of reducing or transforming sulphides, thiols, other sulphur containing compounds, phenols, hydrocarbons, naphthenic acids and their derivatives in spent caustic.

Yet another embodiment of the present invention provides haloalkaliphilic consortium of bacteria wherein the said haloalkaliphilic consortium is capable of treating spent caustic.

Yet another embodiment of the present invention provides use of haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) capable of reducing or transforming sulphides, thiols, other sulphur containing compounds, phenols, hydrocarbons, naphthenic acids and their derivatives in spent caustic.

Yet another embodiment of the present invention provides use of two or more haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) capable of reducing or transforming sulphides, thiols, other sulphur containing compounds, phenols, hydrocarbons, naphthenic acids and their derivatives in spent caustic.

Yet another embodiment of the present invention provides use of haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) in a method for reducing or transforming sulphides, thiols, other sulphur containing compounds, phenols, hydrocarbons, naphthenic acids and their derivatives in spent caustic.

Yet another embodiment of the present invention provides use of two or more haloalkaliphilic bacterial consortium selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus* sp. (MTCC 5666) in a method for reducing or transforming sulphides, thiols, other sulphur containing compounds, phenols, hydrocarbons, naphthenic acids and their derivatives in spent caustic.

In another aspect of the method of present invention the treatment of spent caustic with haloalkaliphilic bacterial consortium is carried out at percentage of saturated oxygen, wherein the percentage of oxygen saturation can be extensively varied at the start or initial stage of the treatment as well at the later stage of the treatment, as discussed below. The said aspect of the invention has been demonstrated in Examples 4 and 6.

(i) At the start of the treatment the oxygen saturation can be maintained as low as in the range of 0-20% followed by higher oxygen saturation in the range of 60-100%; or (ii) At the start of the treatment the oxygen saturation can maintained as high as in the range of 60-100% followed by lowering of the oxygen saturation in the range of 0-20%.

Another embodiment of the present invention provides a method as herein described wherein the percentage of saturated oxygen in the reactor is initially maintained as low as in the range of 0-20% followed by a higher percentage of saturated oxygen in the range of 60-100% (Example 4).

Yet another embodiment of the present invention provides a method as herein described wherein the percentage of saturated oxygen in the reactor is maintained for 5-48 hrs at 0-20% saturation followed by 60-100% saturation for 10-48 hrs.

Yet another embodiment of the present invention provides a method as herein described wherein the percentage of saturated oxygen in the reactor is maintained for 30 hrs at 10% saturation followed 100% saturation for 30 hrs.

Another embodiment of the present invention provides a method as herein described wherein the percentage of saturated oxygen in the reactor is maintained for 5-48 hrs at 60-100% saturation followed by 0-20% saturation for 10-48 hrs.

Yet another embodiment of the present invention provides a method as herein described wherein the percentage of saturated oxygen is the reactor is maintained for a week at 0-20% saturation followed by 60-100% saturation.

In another aspect the present invention provides a method wherein the treatment of spent caustic can be carried out in a single reactor or two reactors. When the reaction is carried out in two reactors then product of first reactor is transferred to the second reactor. In case of two reactor both reactors are maintained at different oxygen saturation concentrations i.e. in the first reactor the oxygen saturation is in the range of 0-20% saturation and in the second reactor the oxygen saturation is in the range of 60-100% saturation.

Further another aspect of the present invention provides that when reaction is carried in two reactors in series then the reaction is run in continuous mode, whereas when the reaction is carried out in a single reactor the reaction is run in batch mode.

Another aspect of the present invention provides a reactor system in which the exhaust gas that is stripped from the reactor suspension, containing volatile compounds like sulfur dioxide, hydrogen sulfide, hydrocarbons and their and metabolites are continuous recycled to the reactor after condensing them in a condenser maintained at temperature of 5° C.

In another aspect the present invention provides a bio-assisted method wherein the disposal and regeneration of spent caustic is performed at an ambient temperature and pressure.

Yet another embodiment of the present invention after treatment of the spent caustic the biomass can be recovered by suitable technique like centrifugation, filtration and the recovered biomass can be re-used for treatment of fresh spent caustic.

Another aspect of the present invention provides a method as herein described wherein the mixture of spent caustic and haloalkaliphilic consortium treated in batch mode as well as continuous mode using a stirrer reactor, up-flow reactor and such suitable reactor.

In another embodiment the present invention provides a method in which after treatment of spent caustic using the haloalkaliphilic consortium as herein described in present invention the recovered caustic free of contaminants can be used for various purposes like maintenance of pH of ETPs, removal of contaminants from gaseous and hydrocarbon streams.

Another aspect of the present invention provides a method of treatment of spent caustic as herein described wherein the method uses a nutrient system consisting of $K_2HPO_4$ (4-10 g/l), $KH_2PO_4$ (4-10 g/l), $MgCl_2$ (0.2-2 g/l), 0.5-2 ml trace elements, sodium carbonate (2-20 g/l), yeast extract (4-10 g/l), ammonium nitrate (5-8 g/l), citrate (10-20 g/l), sorbitol ester (5-25 ppm), Oleic acid (100-1000 ppm), pantothenic acid (20-500 ppm), thiamine (25-300 ppm). The trace element solution (gram per liter) comprises nitrilotriacetic acid (1.0), $FeSO_4.7H_2O$ (0.01), $MnCl_2.4H_2O$ (0.005), $CoCl_2.6H_2O$ (0.09), $CaCl_2.2H_2O$ (0.9), $ZnCl_2$ (0.55), $CuCl_2.H_2O$ (0.03), $H_3BO_3$ (0.02), $Na_2MoO_4$ (0.02).

The invention will now be explained with the help of following examples. However, the scope of the invention should not be limited to these examples as the person skilled in the art can easily vary the proportion of the ingredients and combinations.

Example 1: Isolation of the Microbes

The Microbes were Isolated by Enrichment:

Microbes were isolated through enrichment culture techniques and directed forced evolution. Briefly, to isolate the microbes with desired traits activated sludge from aeration tank of refinery (Indian Oil, Panipat Refinery Panipat, Haryana, India) effluent treatment plant was added to spent caustic obtained from refinery after amending with growth supplements. The growth supplements contained (g/l) $Na_2CO_3$ (5), $NaHCO_3$ (2.5) $KH_2PO_4$ (4), $K_2HPO_4$ (1), $MgSO_4$ (1.0), $(NH_4)_2SO_4$ (0.50), $KNO_3$ (2.0), $ZnSO_4$ (0.5), yeast extract (4), and trace element (2 ml solution). The trace element solution (gram per liter) comprises Nitrilotriacetic acid (1.0), $FeSO_4.7H_2O$ (0.01), $MnCl_2.4H_2O$ (0.005), $CoCl_2.6H_2O$ (0.02), $CaCl_2.2H_2O$ (0.5), $ZnCl_2$ (0.15), $CuCl_2.H_2O$ (0.03), $H_3BO_3$ (0.02), $Na_2MoO_4$ (0.02), $Na_2SeO_3$ (0.02), $NiSO_4$ (0.03), $SnCl_2$ (0.03). The contaminants present spent caustic served as only source of carbon and energy. The culture system incubated aerobically at temperature ranging from 30-50° C. At weekly interval it was transfer to fresh media also using refinery spent caustic as sole carbon and energy source. This was repeated for 7 cycles and subsequently microbes were isolated on agar plate having pH 14 and salinity 4%. The bacterial colonies appeared on the agar plate were further purified. Subsequently, individual bacteria are grown on refinery spent caustic and its growth is evaluated at timed interval by measuring colony forming units (CFU) on agar plate. Bacteria are selected for further studies based on their ability to grow faster and degrade at least one of the contaminants at high pH and salinity. The bacteria which were found suitable for the present invention comprises of *Pseudomonas stutzeri* (MTCC 25027), *Arthobacter* sp. (MTCC 25028), *Bacillus subtilis* (MTCC 25026), *Achromobacter xylooxidan* (MTCC 25024). These bacteria were used in combination with hydrocarbon degrading *Bacillus substilis* (MTCC 5386), *Pseudomonas aeruginosa* (MTCC 5389) and *Lysinibacillus* sp. (MTCC 5666).

The foresaid microbes have been deposited with the Microbial Type Culture Collection (MTCC), Chandigarh, India as required under the Budapest Treaty and have been assigned there respective Accession numbers as recited above.

Example 2: Development of the Consortia

Based on growth ability, a combination of bacteria including *Pseudomonas stutzeri* (MTCC 25027), *Arthobacter* sp. (MTCC 25028), *Bacillus subtilis* (MTCC 25026), *Achromobacter xylooxidan* (MTCC 25024), *Lysinibacillus* sp. (MTCC 5666) are developed. The consortium showed synergistic effect in terms of degradation of contaminants present in spent caustic as represented in Table 1.

TABLE 1

The effect of Haloalkaliphilic bacterial consortium

| S. No. | Bacteria/mixture | % hydrocarbon degradation in 50 hr | % phenol degradation in 50 hr |
|---|---|---|---|
| 1 | *Pseudomonas stutzeri* (MTCC 25027), | 63.3 | 23.4 |
| 2 | *Arthobacter* sp. (MTCC 25028), | 42.2 | 52.8 |
| 3 | *Bacillus subtilis* (MTCC 25026), | 71.1 | 45.1 |
| 4 | *Achromobacter xylooxidan* (MTCC 25024) | 56.6 | 23.8 |
| 5 | *Lysinibacillus* sp. (MTCC 5666) | 51.2 | 43.6 |
| 6 | Consortium/Mixture of above bacteria (as mentioned in S. Nos. 1-6 above) in equal proportion | 97.9 | 99.2 |

The Haloalkaliphilic bacterial consortium was evaluated in shake flask at 35° C. and 120 rpm actual spent caustic obtained from refinery. The control without inoculation is used as negative control and is run under similar conditions. At the time interval samples are taken and analyzed for CFU/ml on agar plate as well for concentration of contaminant by suitable analytical techniques. The Haloalkaliphilic bacterial consortium also can be used in immbolized form or in free form. The Haloalkaliphilic bacterial consortium can be immobilized varieties of membranes such as synthetic plastics, surface-modified carbon nanotubes, poly (tetrafluoroethylene) (PTFE) fibrils, zeolite, clay, anthracite, porous glass, activated charcoal, ceramics, acrylamide, polyurethane, polyvinyl, resins and natural polymer etc. The advantage of using Haloalkaliphilic bacterial consortium in an immobilized form provides enhanced microbial cell stability, allows continuous process operation and prevents the requirement to separate the biomass-liquid separation requirement. The immobilization can be done as per the method known in prior art.

Example 3: Treatment in Bioreactor

The spent caustic is fed in a CSTR with air bubbling system reactor and to the reactor nutrient system containing $K_2HPO_4$ (4 g/l), $KH_2PO_4$ (4 g/l), $MgCl_2$ (0.2 g/l), 0.5 g/l of trace elements, sodium carbonate (2 g/l), yeast extract (5 g/l), sodium nitrate (4 g/l), citrate (5-10 g/l), sorbitol ester (5 ppm), Oleic acid (100 ppm), pantothenic acid (20 ppm), thiamine (25 ppm) was added. The reactor is inoculated with haloalkaliphilic microbial consortium to the cell concentration of $10^2$ CFU/ml. The spent caustic was treated as received from an oil refinery and reactor was run at ambient temperature. The % of oxygen saturation of the reactor was maintained initially for 30 hr at 10% saturation followed by saturation at 100% level. The stirring of the reactor was adjusted at 50 rpm for initial 30 hrs followed by 800 rpm for next 30 hrs. To prevent the release of volatile compounds from the system, gas phases are continuously recycled. The recycled gas is first passed to a condenser (maintained at 5° C.) to recover the volatile compounds and metabolites. A control without bacteria was also run under similar conditions. The treatment was done without sterilizing the spent caustic.

At the time interval samples are taken and analyzed for CFU/ml on agar plate as well for concentration of contaminant by suitable analytical techniques as represented in Table 2.

TABLE 2

Haloalkaliphilic bacterial consortium count during contaminant removal process in refinery spent caustic

| Time (in hrs) | Control without inoculation | Inoculated with microbial consortia |
|---|---|---|
| 0 | Nil | 7.20E+02 |
| 10 | Nil | 8.90E+07 |
| 20 | Nil | 7.80E+08 |
| 30 | Nil | 3.20E+11 |
| 40 | Nil | 3.80E+12 |
| 50 | Nil | 7.60E+14 |
| 60 | Nil | 8.80E+14 |

Table-2 shows the time dependent growth of the Haloalkaliphilic bacterial consortium indicating that they utilize contaminates present in the spent caustic as carbon and energy source. In the control almost no growth of bacteria was found up which showed that indigenous Haloalkaliphilic bacterial consortium has no role in the contaminant removal which is further corroborated by decrease in the concentration of the contaminates removal in the system where microbial consortia was added (Table-3).

The treated spent caustic has more than 98% reduction in total sulfur, sulphides, mercaptans, hydrocarbon, phenol and other contaminants in comparison to abiotic control without the Haloalkaliphilic bacterial consortium (as represented in Table 3). The pH of the reactor with Haloalkaliphilic bacterial consortium was 13 in comparison to 14 in abiotic control after 60 hrs. The treated spent caustic is centrifuged at 8000 rpm for 10 min and biomass s removed. Such obtained cell and contaminant free caustic can be reused. The biomass obtained after centrifugation is used for treatment of another batch of the spent caustic.

TABLE 3

The contaminant removal in refinery spent caustic

| | % degradation | | | | | | | |
|---|---|---|---|---|---|---|---|---|
| | Thiol | | Merceptans | | Phenol | | sulphides | |
| Time (hrs.) | Control without microbial consortia | With microbial consortia | Control without microbial consortia | With microbial consortia | Control without microbial consortia | With microbial consortia | Control without microbial consortia | With microbial consortia |
| 10 | 0.1 | 33.2 | 0.1 | 28.3 | 0 | 43.4 | 1 | 32.4 |
| 20 | 0.2 | 75.4 | 0.2 | 70.4 | 0 | 63.6 | 2 | 43.8 |
| 30 | 0.2 | 92.4 | 0.3 | 90.7 | 0.1 | 93.4 | 3.1 | 67.5 |
| 40 | 0.6 | 97.7 | 0.7 | 87.4 | 0.3 | 95.8 | 3.3 | 85.4 |
| 50 | 1 | 97.9 | 2 | 95.6 | 0.4 | 99.4 | 3.4 | 99.4 |

TABLE 3-continued

The contaminant removal in refinery spent caustic

| | % degradation | | | | | |
|---|---|---|---|---|---|---|
| | Hydrocarbon | | Benzene | | Naphthenic acid | |
| Time (hrs.) | Control without microbial consortia | With microbial consortia | Control without microbial consortia | With microbial consortia | Control without microbial consortia | With microbial consortia |
| 10 | 1.4 | 40.3 | 1.9 | 47.8 | 0 | 47.3 |
| 20 | 1.9 | 65.5 | 2.4 | 51.4 | 0 | 54.7 |
| 30 | 3.5 | 78.6 | 3.1 | 67.7 | 0 | 78.2 |
| 40 | 3.7 | 96.8 | 3.4 | 95.8 | 0.1 | 92.1 |
| 50 | 3.9 | 99.2 | 4.9 | 99.4 | 0.5 | 97.4 |

Example 4: Bio-Assisted Method Using with Two Reactors (with Free Form Haloalkaliphilic Bacterial Consortium)

Treatment is done in two continuously fed systems consisting of two CSTRs in series. The spent caustic is fed in the first reactor (2 L volume) along with nutrient system consisting of $K_2HPO_4$ (4 g/l), $KH_2PO_4$ (4 g/l), $MgCl_2$ (0.2 g/l), 0.5 g/l of trace elements, sodium carbonate (5 g/l), yeast extract (7 g/l), ammonium nitrate (8 g/l), citrate (8 g/l), sorbitol ester (5 ppm), Oleic acid (230 ppm), pantothenic acid (20 ppm), thiamine (25 ppm).

The first reactor (2 L volume) was operated as 40° C. and inoculated with microbial consortium to obtain the cell count of >$10^2$ CFU/ml and allowed to grow for 24 hrs. Subsequently, the spent caustic solution was continuously fed with HRT of 24 hrs.

The percentage oxygen saturation in the first reactor was maintained 20% maintain by sparging the air and it was stirred at 100 rpm. The effluent of first reactor was introduced in the second CSTR where the percentage of oxygen saturation level in the second reactor was maintained at 80% with stirring of 500 rpm. The second reactor was operated at ambient temperature and pressure. The HRT of the second reactor was 24 hrs.

To prevent the release of VOC from the system, the exhaust gas from the reactor was continuously recycled to the reactor. The recycled gas first passed a condenser to recover VOC and the fed to the same reactor. A control without microbes was run parallel. Un-treated and treated were analyzed for contaminant level using appropriate analytical tools. The results are shown in Table 4.

TABLE 4

Treatment of spent caustic with free form haloalkaliophilic bacterial consortium

| | Content in % | |
|---|---|---|
| Contaminant | After treatment with Haloalkaliphilic bacterial consortium | Control without Haloalkaliphilic bacterial consortium |
| Total sulfur | 0.012 | 2.69 |
| Sulphides | 0.003 | 1.67 |
| Mercaptans | 0.017 | 2.62 |
| Phenol | 0.0002 | 0.020 |
| Hydrocarbons | 0.0001 | 0.32 |
| Naphthenic acid | 0.0002 | 0.024 |

Example 5: Bio-Assisted Method Using with Two Reactors (with Immobilized Haloalkaliphilic Bacterial Consortium)

Treatment is done in two continuously fed system consisting of two CSTRs in series as in the example-3 the consortia used in both CSTR was immobilized in porous glass and 10 ml (20 mg dry wt/ml porous glass) were used as inoculum. Table-5 showed that immobilized cells were equally effective as of free cells.

TABLE 5

Treatment of spent caustic with immobilized cells haloalkaliphilic bacterial consortium

| | Content in % | |
|---|---|---|
| Contaminant | After treatment with haloalkaliphilic bacterial consortium | Control without haloalkaliphilic bacterial consortium |
| Total sulfur | 0.010 | 2.69 |
| Sulphides | 0.002 | 1.67 |
| Mercaptans | 0.018 | 2.62 |
| Phenol | 0.0001 | 0.020 |
| Hydrocarbons | 0.0002 | 0.32 |
| Naphthenic acid | 0.0001 | 0.024 |

Example 6: Bio-Assisted Method Using with Two Reactors (with Free Form Haloalkaliphilic Bacterial Consortium)

Treatment is done in two continuously fed systems consisting of two CSTRs in series. The spent caustic is fed in the first reactor (2 L volume) along with nutrient system consisting of $K_2HPO_4$ (4 g/l), $KH_2PO_4$ (4 g/l), $MgCl_2$ (0.2 g/l), 0.5 g/l of trace elements, sodium carbonate (5 g/l), yeast extract (7 g/l), ammonium nitrate (8 g/l), citrate (8 g/l), sorbitol ester (5 ppm), Oleic acid (230 ppm), pantothenic acid (20 ppm), thiamine (25 ppm). The first reactor (2 L volume) was operated as 40° C. and inoculated with microbial consortium to obtain the cell count of >$10^2$ CFU/ml and allowed to grow for 24 hrs. Subsequently, the spent caustic solution was continuously fed with HRT of 24 hrs. The percentage oxygen saturation in the first reactor was maintained 80% maintain by sparging the air and it was stirred at 1000 rpm. The effluent of first reactor was introduced in the second CSTR where the percentage of oxygen saturation level in the second reactor was maintained at 20% with stirring of 200 rpm. The second reactor was operated at ambient temperature and pressure. The HRT of the second reactor was 24 hrs. To prevent the release of VOC from the system, the exhaust gas from the reactor was continuously recycled to the reactor. The recycled gas first passed a condenser to recover VOC and the fed to the same reactor. A control without microbes was run parallel. Un-treated and treated were analyzed for contaminant level using appropriate analytical tools. The results are shown in table-5.

TABLE 6

Treatment of spent caustic with free form haloalkaliphilic bacterial consortium

| Contaminant | Content in % | |
|---|---|---|
| | After treatment with microbial blend | Control without microbial blend |
| Total sulfur | 0.012 | 2.98 |
| Sulphides | 0.002 | 2.17 |
| Mercaptans | 0.019 | 3.69 |
| Phenol | 0.0002 | 0.050 |
| Hydrocarbons | 0.0001 | 0.67 |
| Napthenic acid | 0.0003 | 0.076 |

ADVANTAGES

The method of treatment of spent caustic of the present invention does not require efforts for maintaining critical parameters of pH as compared to that of the prior art wherein pH is maintained by addition of acids.

Further, treated spent caustic can be used for industrial applications by supplementing with minimum amount of solid metal hydroxide for treating oil and gas streams, maintenance of pH of ETP, paper and pulp industry etc.

The microbial consortia and its mediated process used in the present invention can degrade/transform multiple contaminants from the spent caustic in contrast to prior art wherein sulfides are treated in particular.

Also, said microbial consortia can be easily reproduced and does not require acclimatization.

We claim:

1. A bio-assisted method of treating spent caustic using a haloalkaliphilic bacterial consortium, said method comprises the steps of:
   (a) mixing the spent caustic with a haloalkaliphilic bacterial consortium including at least two microbes selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389) and *Lysinibacillus* sp. (MTCC 5666) in a reactor;
   (b) maintaining the percentage of saturated oxygen in the reactor initially in the range of 0-20% or 60-100% saturation for 48 hrs followed by saturated oxygen in the range of 60-100% or 0-20% for 24-48 hrs respectively;
   (c) carrying out the reaction of steps (a) and (b) for about 3-5 days; and
   (d) obtaining caustic with reduced concentration of sulphides, thiols, other sulphur containing compounds, phenols, hydrocarbons, naphthenic acids and their derivatives.

2. The method as claimed in claim 1, wherein in step (a) is performed at the pH in the range of 8 to 13.

3. The method as claimed in claim 1, wherein in step (b) the saturated oxygen in the reactor is initially maintained in the range of 0-20% followed by saturated oxygen maintained in the range of 60-100%.

4. The method as claimed in claim 1, wherein in step (b) the saturated oxygen in the reactor is initially maintained in the range of 60-100% followed by saturated oxygen maintained in the range of 0-20%.

5. The method as claimed in claim 1, wherein the haloalkaliphilic bacterial consortium is present in a concentration of at least $10^2$ CFU/ml.

6. The method as claimed in claim 1, wherein said method is done either in the same reactor by altering the air saturation after a certain time or in a two series reactor where effluent of one reactor works as influent to another reactor and both reactors have different air saturation levels.

7. The method as claimed in claim 1, wherein the haloalkaliphilic bacterial consortium is used in immobilized or free form.

8. The method as claimed in claim 1, wherein said method is performed in batch mode or continuous mode using a continuously stirred reactor, up-flow reactor or any such suitable continuous mode reactor.

9. The method as claimed in claim 1, wherein the haloalkaliphilic bacterial consortium is immobilized when the reaction is carried out in a continuous mode.

10. The method as claimed in claim 1, wherein the reaction is carried out in a single reactor or two reactors.

11. A formulated haloalkaliphilic bacterial consortium including at least two microbes selected from *Pseudomonas stutzeri* (MTCC 25027), *Arthobacter* sp. (MTCC 25028), *Bacillus subtilis* (MTCC 25026), *Achromobacter xylooxidan* (MTCC 25024), *Bacillus substilis* (MTCC 5386), *Pseudomonas aeruginosa* (MTCC 5389), *Lysinibacillus sp.* (MTCC 5666) capable of reducing or transforming sulphides, thiols, other sulphur containing compounds, phenols, hydrocarbons, naphthenic acids and their derivatives in spent caustic.

12. A haloalkaliphilic consortium as claimed in claim 11, wherein said haloalkaliphilic consortium is capable of treating spent caustic.

* * * * *